United States Patent [19]

Acker et al.

[11] Patent Number: 4,508,915
[45] Date of Patent: Apr. 2, 1985

[54] SILYLALKYL THIOALKANOATES AND THEIR USE FOR CONTROLLING UNDESIRABLE PLANT GROWTH

[75] Inventors: Rolf-Dieter Acker, Leimen; Adolf Parg, Bad Duerkheim; Bruno Wuerzer, Otterstadt, all of Fed. Rep. of Germany

[73] Assignee: BASF Aktiengesellschaft, Fed. Rep. of Germany

[21] Appl. No.: 476,578

[22] Filed: Mar. 18, 1983

[30] Foreign Application Priority Data

Mar. 20, 1982 [DE] Fed. Rep. of Germany ....... 3210336

[51] Int. Cl. .............................. C07F 7/08; C07F 7/10
[52] U.S. Cl. ........................................ 556/418; 71/98
[58] Field of Search ............................ 556/418; 71/98

[56] References Cited

U.S. PATENT DOCUMENTS 3,853,935 12/1974 Rosudy et al. ...................... 556/418
4,339,581 7/1982 Tolten et al. .................... 556/418 X
4,349,377 9/1982 Dürr et al. .............................. 71/98

*Primary Examiner*—Paul F. Shaver
*Attorney, Agent, or Firm*—Keil & Weinkauf

[57] ABSTRACT

Silylalkyl thioalkanoates of the formula

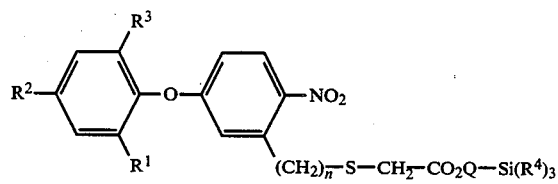

where $R^1$, $R^2$, $R^3$, $R^4$, Q and n have the meanings mentioned in the description, are used for controlling undesirable plant growth.

9 Claims, No Drawings

SILYLALKYL THIOALKANOATES AND THEIR USE FOR CONTROLLING UNDESIRABLE PLANT GROWTH

The present invention relates to silylalkyl thioalkanoates, herbicides which contain these compounds as active ingredients, and the use of the active ingredients or of the herbicides in controlling undesirable plant growth.

It has been disclosed that alkyl phenoxyphenylthioalkanoates are herbicides (Japanese Preliminary Published Application No. 77/21,320).

We have found that silylalkyl thioalkanoates of the formula

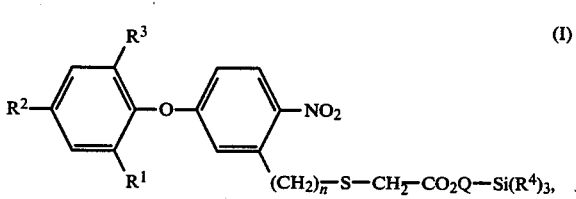

where $R^1$ is hydrogen or halogen, $R^2$ is halogen, trihalomethyl, trihalomethoxy or trihalomethylmercapto, $R^3$ is hydrogen or halogen, the radicals $R^4$ are identical or different and are each $C_1$–$C_6$-alkyl or phenyl, Q is straight-chain or branched $C_1$–$C_8$-alkylene and n is 0 or 1, possess substantial selective herbicidal activity.

In formula I, trihalomethyl, trihalomethoxy and trihalomethylmercapto groups $R^2$ are, for example, trifluoromethyl, trifluoromethoxy or trifluoromethylmercapto, $R^4$ is phenyl or straight-chain or branched $C_1$–$C_6$-alkyl, preferably $C_1$–$C_4$-alkyl, in particular methyl or ethyl, and straight-chain or branched alkylene chains Q of 1 to 8 carbon atoms in total are, for example, methylene, dimethylene, trimethylene, tetramethylene, methylmethylene, 2-methyltrimethylene, 2-methyldimethylene, 1-methyldimethylene, 3-methyltetramethylene, 2-ethyldimethylene, 3-propyltrimethylene, pentamethylene or hexamethylene.

Preferred silylalkyl thioalkanoates of the formula I are those in which $R^2$ is trifluoromethyl or trifluoromethylmercapto.

The silylalkyl thioalkanoates of the formula I are obtained in a conventional manner by reacting a carboxylic acid of the formula

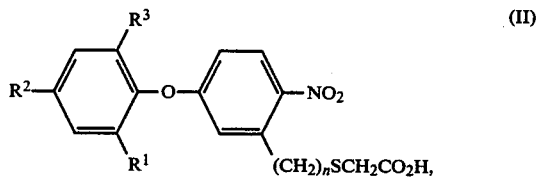

where $R^1$, $R^2$, $R^3$ and n have the above meanings, or a salt of this acid, with a halogenating agent to give the corresponding acyl chloride, and then reacting this, in the presence or absence of an acid acceptor, with a silylalkanol of the formula

  (III), where $R^4$ and Q have the above meanings (version a), or by reacting a carboxylic acid of the formula II with a silylalkanol of the formula III in the presence of an esterifying agent (version b).

Process (a) is carried out using about stoichiometric amounts of the substances, ie. from about 1.0 to 1.3 equivalents of halogenating agent per equivalent of the compound II.

Advantageously, the halogenating agent is added to the compound II, which may or may not be dissolved in an inert solvent, and the mixture is heated at from 50° to 120° C., preferably from 70° to 100° C., for from 0.5 to 3 hours. The volatile constituents are distilled off under reduced pressure, the acyl chloride which remains, in an inert solvent, is then added, a little at a time, to a solution of the silylalkanol of the formula III and an acid acceptor, in amounts corresponding to one equivalent of II per 1.0–1.3 equivalents of the compound III and the acid acceptor, and the mixture is stirred at from 70° to 100° C. for from 1 to 5 hours. The solution is filtered and evaporated down, after which the end product can be purified by recrystallization or chromatography.

Suitable acid acceptors are the bases conventionally used for this purpose. These preferably include tertiary amines, alkaline earth metal compounds, ammonium compounds, alkali metal compounds and mixtures of any of these, as well as zinc compounds. Examples are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc acetate, sodium formate, sodium acetate, trimethylamine, triethylamine, tripropylamine, triisopropylamine, tributylamine, triisobutylamine, tri-sec-butylamine, tri-tert.-butylamine, tribenzylamine, tricyclohexlamine, triamylamine, diisopropylethylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N'-dimethylcyclohexylamine, 2,6-lutidine, 2,4-lutidine, trifurylamine and triethylenediamine.

Process (b) is carried out using about stoichiometric amounts of substances, ie. from about 0.8 to 1.3 equivalents of the compound II per equivalent of the compound III, and it is advantageous to add an esterifying agent, eg. carbonyldiimidazole, sulfonyldiimidazole or cyclohexylcarbodiimide, in an amount of from 0.5 to 2.5 equivalents. After the compounds of the formula II and III and the esterifying agent have been combined at from −20° to +50° C., stirring is continued for from 5 to 25 hours, the mixture is filtered and evaporated down, and the end product thus obtained can then be purified by recrystallization or chromatography.

In both versions of the process, solvents which are inert under the reaction conditions are used. Examples of suitable solvents are aliphatic and aromatic halohydrocarbons, in particular chlorohydrocarbons, eg. tetrachloroethylene, 1,1,2,2- and 1,1,1,2-tetrachloroethane, dichloropropane, methylene chloride, dichlorobutane, chloroform, chloroanaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene, ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether, nitrohydrocarbons, eg. nitromethane, nitroethane, nitrobenzene, o-, m- and p-chloronitrobenzene and o-nitrotoluene, nitriles, eg. acetonitrile, butyronitrile, isobutyronitrile, benzonitrile and m-chlorobenzonitrile, aliphatic and cycloaliphatic hydrocarbons, eg. heptane, pinane, nonane, o-, m- and p-cymene, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane, esters, eg. ethyl acetate, ethyl acetoacetate and isobutyl acetate, amides, eg. formamide, methylformamide and dimethylformamide, ketones, eg. acetone and methyl ethyl ketone, and mixtures of any of these solvents. Advantageously, the solvent is used in an amount of from 100 to 2,000, preferably from 200 to 700, % by weight, based on the starting materials.

Both processes can be carried out continuously or batchwise, under atmospheric or superatmospheric pressure. For the sake of simplicity, atmospheric pressure is preferably employed.

The Examples which follow illustrate the preparation of the novel substances. Parts are by weight.

EXAMPLE 1

20.1 parts of 2-[5-(4'-trifluoromethyl-2'-chlorophenoxy)-2-nitrobenzylthio]-acetic acid in 80 parts of toluene were refluxed with 6.0 parts of thionyl chloride for 2 hours. The mixture was cooled, volatile constituents were distilled off under reduced pressure, the residue was then taken up in 25 parts of toluene, and the solution was added, a little at a time, to 6.1 parts of trimethylsilylethanol, 7.1 parts of triethylamine and 10 parts of toluene at from 25° to 30° C. Stirring was continued for 3 hours at room temperature, after which the solution was evaporated down and the residue was chromotographed over silica gel with toluene/acetone (70/30). 15 parts of 2-trimethylsilylethyl 2-[5-(4-trifluoromethyl-2-chlorophenoxy)-2-nitrobenzylthio]-acetate of $n_D^{22}=1.5525$ were obtained (Compound No. 11).

EXAMPLE 2

12.2 parts of 2-[5-(4'-trifluoromethyl-2'-chlorophenoxy)-2-nitrophenylthio]-acetic acid and 30 parts of acetonitrile were initially taken, and 4.8 parts of pyridine and 5.3 parts of 4-trimethylsilyl-n-butanol were added. Stirring was continued for 10 minutes at from 0° to 5° C., 3.6 parts of dicyclohexylcarbodiimide were then added a little at a time, and stirring was continued at 0° C. for 12 hours. 1.0 part of 0.5 molar oxalic acid in dimethylformamide was added, the mixture was left to stand for 30 minutes, the precipitate was filtered off, the filtrate was evaporated down and the oil obtained was triturated with cyclohexane. 8.1 parts of 4-trimethylsilyl-n-butyl 2-[5-(4-trifluoromethyl-2-chlorophenoxy)-2-nitrophenylthio]-acetate of melting point 78°–81° C. were obtained (Compound No. 7).

The following silylalkyl thioalkanoates of the formula I were, or may be, obtained by a similar procedure:

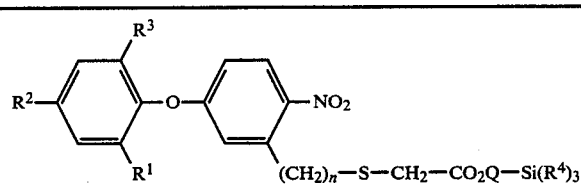

| No. | R¹ | R² | R³ | R⁴ | n | Q | M.p. [°C.]/$n_D$ |
|---|---|---|---|---|---|---|---|
| 1 | Cl | F₃C | H | CH₃ | 0 | —CH₂— | 1.5587 |
| 2 | Cl | F₃C | H | CH₃ | 0 | —CH₂CH₂— | 57–58 |
| 3 | Cl | F₃C | H | CH₃ | 0 | —CH₂CH₂CH₂— | 1.5568 |
| 4 | Cl | F₃C | H | CH₃ | 0 | —CH₂—CH(CH₃)CH₂— | |
| 5 | Cl | F₃C | H | CH₃ | 0 | —CH₂CH(CH₃)— | |
| 6 | Cl | F₃C | H | CH₃ | 0 | —CH(CH₃)CH₂— | |
| 7 | Cl | F₃C | H | CH₃ | 0 | —CH₂CH₂CH₂CH₂— | 78–81 |
| 8 | Cl | F₃C | H | CH₃ | 0 | —CH₂CH₂CH(CH₃)CH₂— | |
| 9 | Cl | F₃C | H | CH₃ | 0 | —CH₂CH₂CH₂CH₂CH₂— | |
| 10 | Cl | F₃C | H | CH₃ | 1 | —CH₂— | |
| 11 | Cl | F₃C | H | CH₃ | 1 | —CH₂CH₂— | |
| 12 | Cl | F₃C | H | CH₃ | 1 | —CH₂—CH(CH₃)— | |
| 13 | Cl | F₃C | H | CH₃ | 1 | —CH₂CH₂CH₂— | |
| 14 | Cl | F₃C | H | CH₃ | 1 | —CH₂CH₂CH₂CH₂— | |
| 15 | Cl | F₃C | H | C₂H₅ | 0 | —CH₂— | |
| 16 | Cl | F₃C | H | C₂H₅ | 0 | —CH₂CH₂— | |
| 17 | Cl | F₃C | H | C₂H₅ | 0 | —CH₂CH₂CH₂CH₂— | |
| 18 | Cl | F₃C | Cl | CH₃ | 0 | —CH₂CH₂CH₂— | |
| 19 | Cl | F₃C | Cl | CH₃ | 1 | —CH₂— | |
| 20 | Cl | F₃C | Cl | CH₃ | 0 | —CH(CH₃)— | |

-continued

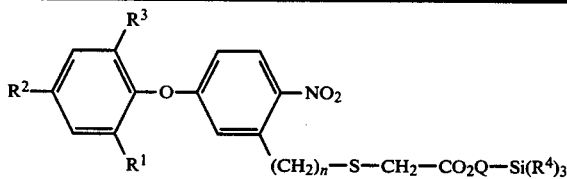

(CH$_2$)$_n$—S—CH$_2$—CO$_2$Q—Si(R$^4$)$_3$

| No. | R$^1$ | R$^2$ | R$^3$ | R$^4$ | n | Q | M.p. [°C.]/n$_D$ |
| --- | --- | --- | --- | --- | --- | --- | --- |
| 21 | Cl | F$_3$C | H | CH$_3$ | 0 | —CH(CH$_3$)— | |
| 22 | Cl | F$_3$C | H | C$_6$H$_5$ | 0 | —CH$_2$— | |
| 23 | Cl | F$_3$C | H | C$_6$H$_5$ | 0 | —CH$_2$CH$_2$— | |
| 24 | Cl | F$_3$CS | H | CH$_3$ | 0 | —CH$_2$— | |
| 25 | Cl | F$_3$CS | H | CH$_3$ | 1 | —CH$_2$CH$_2$— | |

The compounds of the formula I, and acid addition salts thereof, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts or sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 7 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 11 is intimately mixed with 97 parts by weight of particulate kaolin. A dust is obtained containing 3% by weight of the active ingredient.

VII. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 3 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. Preferably, the novel active ingredients are applied after emergence of the unwanted plants. If certain crops plants tolerate the active ingredients less well, application technique may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved and the growth stage of the plants, and varies from 0.005 to 5 kg/ha and more, but is preferably from 0.03 to 3.0 kg/ha.

The herbicidal action of compounds of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated, The soybean plants used for the postemergence treatment were grown in a peat-enriched substrate to ensure better growth than is possible in a sandy loam. The rice plants were also grown in a peat-enriched substrate. No impairment of the results need be feared because the treatments are foilage (postemergence) treatments. For this treatment, either plants which had been sown directly in the pots and grown there were selected, or plants which had been grown separately as seedlings and transplanted to the experiment vessels a few days before treatment. No covers were placed on the pots in this treatment method. The application rates for postemergence treatment varied from ingredient to ingredient, and were from 0.03 to 0.125 kg of active ingredient per hectare.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The test plants employed were Amaranthus spp., *Arachys hypogaea, Chenopodium album, Datura stramonium, Euphorbia geniculata, Glycine max., Lamium purpureum, Oryza sativa, Sinapis alba, Solanum nigrum, Triticum aestivum* and Veronica spp.

The agent used for comparison purposes is the prior art compound ethyl 5-(4′-trifluoromethyl-2′-chlorophenoxy)-2-nitrophenylthioacetate (A) (Japanese Laid-Open Application No. 77/21320).

On investigations into herbicidal action on preemergence applications at rates of 3.0 kg/ha, for example compounds nos. 1, 2, 3 and 7 had a very good action on broadleaved plants.

On investigations into selective herbicidal properties on postemergence application, for instance compounds nos. 1, 2 and 11, at 0.03, 0.125 and 0.06 kg/ha, combated a number of broadleaved weeds very well. The compounds of the formula I are tolerated by rice and wheat much better than comparative agent A. Compound no. 2, at 0.03 kg/ha, results in very slight leaf damage to soybeans.

In view of the many application methods possible, the compounds according to the invention may be used in a large number of crop plants for removing unwanted plant growth.

The following crop plants may be mentioned by way of example:

| Botanical name | Common name |
|---|---|
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napobrassica* | turnips |
| *Brassica napus* var. *rapa* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica (Coffea canephora,* | coffee plants |

| Botanical name | Common name |
| --- | --- |
| Coffea liberica) | |
| Cucumis melo | melons |
| Cucumis sativus | cucumbers |
| Cynodon dactylon | Bermudagrass in turf and lawns |
| Elais guineensis | oil palms |
| Fragaria vesca | strawberries |
| Glycine max | soybeans |
| Gossypium hirsutum | cotton |
| (Gossypium arboreum | |
| Gossypium herbaceum | |
| Gossypium vitifolium) | |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp | apple trees |
| Manihot esculenta | cassava |
| Medicago sativa | alfalfa (lucerne) |
| Mentha piperita | peppermint |
| Musa spp. | banana plants |
| Nicothiana tabacum | tobacco |
| (N. rustica) | |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum | parsley |
| spp. tuberosum | |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays (post-directed) | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A silylalkyl thioalkanoate of the formula

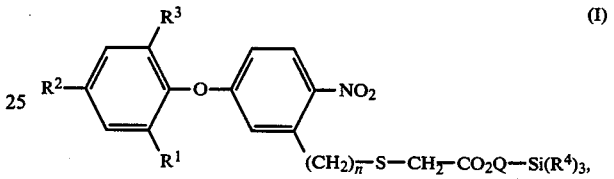

where $R^1$ is hydrogen or halogen, $R^2$ is halogen, trihalomethyl, trihalomethoxy or trihalomethylmercapto, $R^3$ is hydrogen or halogen, the radicals $R^4$ are identical or different and are each $C_1$-$C_6$-alkyl or phenyl, Q is straight-chain or branched $C_1$-$C_8$-alkylene and n is 0 or 1.

2. A silylalkyl thioalkanoate of the formula I as claimed in claim 1, where $R^2$ is trifluoromethyl.

3. Trimethylsilylmethyl 2-[5-(4-trifluoromethyl-2-chlorophenoxy)-2-nitrophenylthio]-acetate.

4. (2-Trimethylsilylethyl)2-[5-(4-trifluoromethyl-2-chlorophenoxy)-2-nitrophenylthio]-acetate.

5. A herbicide containing inert additives and a silylalkyl thioalkanoate of the formula I as claimed in claim 1.

6. A herbicide as claimed in claim 5, where the silylalkyl thioalkanoate of the formula I is one in which $R^2$ is trifluoromethyl.

7. A herbicide as claimed in claim 5, containing trimethylsilylmethyl 2-[5-(4-trifluoromethyl-2-chlorophenoxy)-2-nitrophenylthio]-acetate.

8. A herbicide as claimed in claim 5, containing (2-trimethylsilylethyl)2-[5-(4-trifluoromethyl-2-chlorophenoxy)-2-nitrophenylthio]-acetate.

9. A process for combating the growth of unwanted plants, wherein a herbicidally effective amount of a silylalkyl thioalkanoate of the formula I as claimed in claim 1 is allowed to act on the plants and/or their location.

* * * * *